United States Patent
Marzi et al.

(10) Patent No.: US 7,498,340 B2
(45) Date of Patent: *Mar. 3, 2009

(54) ESTERS IN POSITION 20 OF CAMPTOTHECINS

(75) Inventors: Mauro Marzi, Rome (IT); Domenico Alloatti, Rome (IT); Claudio Pisano, Rome (IT); Maria Ornella Tinti, Rome (IT); Loredana Vesci, Rome (IT); Franco Zunino, Milan (IT)

(73) Assignees: Sigma-Tau Industrie Farmaceutiche Riunite S.p.A., Pomezia (Rome) (IT); Istituto Nazionale per Lo Studio E La Cura Dei Tumori, Milan (IT)

(*) Notice: Subject to any disclaimer, the term of this patent is extended or adjusted under 35 U.S.C. 154(b) by 0 days.

This patent is subject to a terminal disclaimer.

(21) Appl. No.: 11/783,495

(22) Filed: Apr. 10, 2007

(65) Prior Publication Data
US 2007/0213353 A1    Sep. 13, 2007

Related U.S. Application Data

(62) Division of application No. 10/512,094, filed as application No. PCT/IT03/00329 on May 28, 2003, now Pat. No. 7,452,900.

(30) Foreign Application Priority Data
May 31, 2002    (IT)    .................. RM2002A0306

(51) Int. Cl.
*A61K 31/4745*    (2006.01)
*C07D 491/22*    (2006.01)
(52) U.S. Cl. ........................... 514/283; 546/48
(58) Field of Classification Search ........ 514/283; 546/48
See application file for complete search history.

(56) References Cited

U.S. PATENT DOCUMENTS 4,943,579 A    7/1990    Vishnuvajjala et al.
6,242,457 B1    6/2001    Penco et al.

FOREIGN PATENT DOCUMENTS

WO    WO 00/53607    9/2000
WO    WO 01/49691 A    7/2001
WO    WO 01/74402 A2    11/2001

OTHER PUBLICATIONS

Matsumoto, H. et al; "Controlled Drug Release: New Water-Soluble Prodrugs of an HIV Protease Inhibitor"; Bioorg. Med. Chem. Lett., vol. 11, 2001, pp. 605-609, XP002252920.
Database Crossfire Beilstein 'Online!; Beilstein Institut zur Förderung der Chemischen Wissenschaften, Frankfurt am Main, DE; XP002252923; Database Accession Nos. 9312592, 9312810 (BRN's) & Bhatt, R. et al; "Synthesis and in Vivo Antitumor Activity of Poly(L-glutamic acid) Conjugates of 20(S)-Camptothecin"; J. Med. Chem., vol. 46, 2003, pp. 190-193, XP002252921.
Lerchen H-G et al; "Synthesis of 20-0-Linked 20(S)-Camptothecin Glycoconjugates: Impact of the Side Chain of the Ester-Linked Amino Acid on Epimerization during the Acylation Reaction and on Hydrolytic Stability of the Final Glycoconjugates"; Journal Fuer Praktische Chemie, Wiley Vch, Weinheim, DE, vol. 342, No. 8, 2000, pp. 753-760, XP001000978.
Database Crossfire Beilstein 'Online!; Beilstein Institut zur Förderung der Chemischen Wissenschaften, Frankfurt am Main, DE; XP002252922; Database Accession Nos. 7563919, 7967940 (BRN's) & Greenwald, R.B.; "Camptothecin-20-PEG Ester Transport Forms"; Bioorg. Med. Chem., vol. 6, 1998, pp. 551-562, XP000985272.

*Primary Examiner*—Charanjit S Aulakh
(74) *Attorney, Agent, or Firm*—Nixon & Vanderhye P.C.

(57) ABSTRACT

Formula (I) compounds are described: (I) where the groups are as defined in the description here below, the racemic mixtures, their individual enantiomers, their individual diastereoisomers, their mixtures, and their pharmaceutically acceptable salts. Said compounds are topoisomerase I inhibitors.

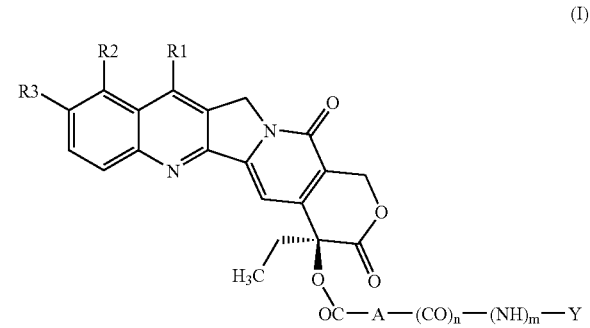

6 Claims, No Drawings

ESTERS IN POSITION 20 OF CAMPTOTHECINS

This application is a divisional of application Ser. No. 10/512,094 filed Oct. 21, 2004 now U.S. Pat. No. 7,452,900, which in turn is the U.S. national phase of international application PCT/IT03/00329 filed 28 May 2003, which designated the U.S. and claims benefit of IT RM2002A000306, dated 31 May 2002, the entire content of which is hereby incorporated by reference.

The invention described herein relates to compounds useful as medicaments, and particularly to derivatives of camptothecin esters in position 20, to processes for their preparation, to their use as active ingredients with topoisomerase 1 inhibiting activity and to pharmaceutical compositions containing them as active ingredients.

BACKGROUND TO THE INVENTION

Camptothecin is an alkaloid isolated by Wall et al. (*J. Am. Chem. Soc.*, 88, 3888-3890 (1966)) for the first time from the tree *Camptotheca acuminata*, a plant native to China, belonging to the Nyssaceae family.

The molecule consists of a pentacyclic structure with a lactone in the E ring, which is essential for cytotoxicity.

For a review of the camptothecins and the problems relating to their use as medicaments, as well as the resolution of a number of such problems, see European Patent EP 1044977, filed in the name of the applicants. Among the preferred compounds of this latter patent we should mention 7-tert-butoxyiminomethyl-camptothecin, which is active orally. Said compound, endowed with substantial activity, cannot be formulated in aqueous liquid compositions, particularly those suitable for the injectable administration route. The problem of the solubility of the camptothecins is well known to experts in the field.

Soluble camptothecin prodrugs are disclosed in U.S. Pat. No. 4,943,579, published on 24 Jul. 1990, which provides esters in position 20 of camptothecins with amino acids directly bound to the hydroxyl of the lactone ring. As discussed in this reference, the problem of making camptothecin and its hydrosoluble derivatives is rendered more difficult by the fact that it is not possible to alter the lactone ring without a loss of therapeutic activity. At the same time, there is, in any event, the problem of reducing the typical toxicity of the camptothecins, particularly at intestinal level. WO 97/21865, The Stehlin Foundation, published on 7 Aug. 1997, provides camptothecin prodrugs for the purposes of prolonging the stability of the lactone ring, which is hydrolysed in vivo, giving rise to an inactive toxic metabolite. To this end, the hydroxy group of the lactone ring is esterified with carboxylic acids of varying length, optionally bearing an epoxide group in the chain. The compounds described in this reference are more liposoluble and are therefore going in a different direction as compared to the present invention. Conover C. D., et al., *Anti-Cancer Drug Design* (1999), 14, 499-506 describe a camptothecin-polyethylene glycol hydrosoluble macromolecular transport system, in which various spacers of an amino acid nature affect its pharmacokinetic and anticancer activity characteristics. WO 00/08033, The University of Kansas, published on 17 Feb. 2000, describes hydrosoluble prodrugs with a sterically hindered hydroxy group, which is esterified with a phosphono-oxymethyl group. Singer J. W., et al., *Journal of Controlled Release*, 74 (2001), 243-247, describe hydrosoluble conjugates of camptothecin with polyglutamic acid-glycine. Matsumoto H., et al., *Bioorganic & Medicinal Chemistry Letters* 11 (2001), 605-609 describe hydrosoluble prodrugs of an HIV virus protease inhibitor (molecule of a dipeptide nature, differing enormously from the molecular structure of camptothecin) and to that end functionalise a hydroxyl group with a portion formed by a spacer part and a solubilising part. The spacer part is provided by a bicarboxylic acid, whereas the solubilising part is provided by a diamine. WO 01/09139, The Stehlin Foundation, published on 8 Feb. 2001, describes aryl esters of camptothecin in position 20, but does not address the problem of hydrosolubility, but rather that of the toxicity and prolonged stability of the lactone ring.

However, much in the design of new drugs various problems are encountered of a physicochemical nature, such as the stability of the molecule in plasma or its hydrosolubility for formulatory purposes, there is a constant search for a better therapeutic index.

SUMMARY OF THE INVENTION

It has now surprisingly been found that esters in position 20 of camptothecins, particularly the camptothecins bearing an oxime group in position 7, as described in the above-mentioned European Patent EP 1044977, are endowed with substantial anticancer activity. These compounds have a better therapeutic index.

The object of the present invention therefore comprises compounds of general formula (I)

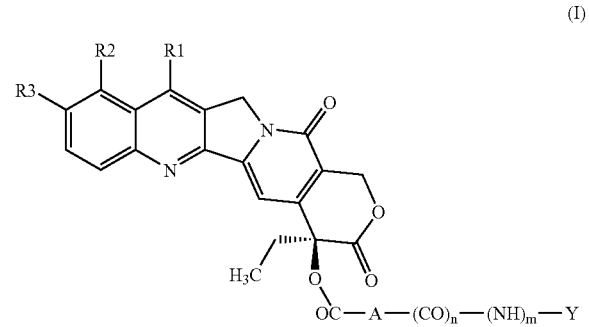

where:

A is saturated or unsaturated straight or branched $C_1$-$C_8$ alkyl, $C_3$-$C_{10}$ cycloalkyl, straight or branched $C_3$-$C_{10}$ cycloalkyl-$C_1$-$C_8$ alkyl; when n and m are equal to 1, then Y is saturated or unsaturated straight or branched $C_1$-$C_8$ alkyl substituted with $NR_{12}R_{13}$ or $N^+R_{12}R_{13}R_{14}$, where $R_{12}$, $R_{13}$ and $R_{14}$, which can be the same or different, are hydrogen or straight or branched $C_1$-$C_4$ alkyl, or Y is BCOOX, where B is a residue of an amino acid, X is H, straight or branched $C_1$-$C_4$ alkyl, benzyl or phenyl, substituted in the available positions with at least one group selected from $C_1$-$C_4$ alkoxy, halogen, nitro, amino, $C_1$-$C_4$ alkyl, or, if n and m are both 0;

Y is 4-trimethylammonium-3-hydroxybutanoyl, both in the form of inner salt and in the form of a salt with an anion of a pharmaceutically acceptable acid, or Y is $N^+R_{12}R_{13}R_{14}$, as defined above;

$R_1$ is hydrogen or a —$C(R_5)$=N—O—$R_4$ group, in which $R_4$ is hydrogen or a straight or branched $C_1$-$C_5$ alkyl or $C_1$-$C_5$ alkenyl group, or a $C_3$-$C_{10}$ cycloalkyl group, or a straight or branched ($C_3$-$C_{10}$) cycloalkyl-($C_1$-$C_5$) alkyl group, or a $C_6$-$C_{14}$ aryl group, or a straight or branched ($C_6$-$C_{14}$) aryl-($C_1$-$C_5$) alkyl group, or a heterocyclic group or a straight or branched heterocyclo-($C_1$-$C_5$) alkyl group, said heterocyclic group containing at least one heteroatom selected from an atom of nitrogen, optionally substituted with a ($C_1$-$C_5$) alkyl group, and/or an atom of oxygen and/or of sulphur; said alkyl, alkenyl, cycloalkyl, cycloalkylalkyl, aryl, arylalkyl, heterocyclic or heterocyclo-alkyl groups may optionally be substituted with one or more groups selected from: halogen, hydroxy, $C_1$-$C_5$ alkyl, $C_1$-$C_5$ alkoxy, phenyl, cyano, nitro, —$NR_6R_7$, where $R_6$ and $R_7$, which may be the same or different, are hydrogen, straight or branched ($C_1$-$C_5$) alkyl, the —COOH group or one of its pharmaceutically acceptable esters; or the —$CONR_8R_9$ group, where $R_8$ and $R_9$, which may be the same or different, are hydrogen, straight or branched ($C_1$-$C_5$) alkyl; or $R_4$ is a ($C_6$-$C_{10}$) aroyl or ($C_6$-$C_{10}$) arylsulphonyl residue, optionally substituted with one or more groups selected from: halogen, hydroxy, straight or branched $C_1$-$C_5$ alkyl, straight or branched $C_1$-$C_5$ alkoxy, phenyl, cyano, nitro, —$NR_{10}R_{11}$, where $R_{10}$ and $R_{11}$, which may be the same or different, are hydrogen, straight or branched $C_1$-$C_5$ alkyl; or $R_4$ is a polyaminoalkyl residue; or $R_4$ is a glycosyl residue; $R_5$ is hydrogen, straight or branched $C_1$-$C_5$ alkyl, straight or branched $C_1$-$C_5$ alkenyl, $C_3$-$C_{10}$ cycloalkyl, straight or branched ($C_3$-$C_{10}$) cycloalkyl-($C_1$-$C_5$) alkyl, $C_6$-$C_{14}$ aryl, straight or branched ($C_6$-$C_{14}$) aryl-($C_1$-$C_5$) alkyl; $R_2$ and $R_3$, which may be the same or different, are hydrogen, hydroxy, straight or branched $C_1$-$C_5$ alkoxy; the N1-oxides, the racemic mixtures, their individual enantiomers, their individual diastereoisomers, their mixtures, and their pharmaceutically acceptable salts.

The present invention comprises the use of the aforesaid formula (I) compounds as active ingredients for medicaments, and particularly for medicaments which are useful as topoisomerase I inhibitors. Among the therapeutic applications deriving from the topoisomerase I inhibiting activity, tumours and parasitic or viral infections should be mentioned.

The present invention comprises pharmaceutical compositions containing formula (I) compounds as active ingredients, in admixture with pharmaceutically acceptable vehicles and excipients.

The present invention also includes the processes for the preparation of formula (I) compounds.

DETAILED DESCRIPTION OF THE INVENTION

Within the framework of the present invention, examples of the straight or branched $C_1$-$C_8$ alkyl group, are understood to include methyl, ethyl, propyl, butyl, pentyl, hexyl, heptyl and octyl and their possible isomers, such as, for example, isopropyl, isobutyl, and ter-butyl.

Examples of the straight or branched $C_1$-$C_5$ alkenyl group are methylidene, ethylidene, vinyl, allyl, propargyl, butylene, and pentylene, where the double carbon-carbon bond may be situated in the various possible positions of the alkylene chain, which can also be branched in the context of the isomery allowed.

Examples of the $C_3$-$C_{10}$ cycloalkyl group are cyclopropyl, cyclobutyl, cyclopentyl, cyclohexyl, cyclooctyl, and polycyclic groups, such as, for example, adamantyl.

Examples of the straight or branched ($C_3$-$C_{10}$) cycloalkyl-($C_1$-$C_5$) alkyl group are cyclopropylmethyl, 2-cyclopropylethyl, 1-cyclopropylethyl, 3-cyclopropylpropyl, 2-cyclopropylpropyl, 1-cyclopropylpropyl, cyclobutylmethyl, 2-cyclobutylethyl, 1-cyclobutylethyl, 3-cyclobutylpropyl, 2-cyclobutylpropyl, 1-cyclobutylpropyl, cyclohexylmethyl, 2-cyclohexylethyl, 1-cyclohexylethyl, 3-cyclohexylpropyl, 2-cyclohexylpropyl, 1-cyclohexylpropyl, 5-cyclohexylpentyl, 3-cyclohexylpentyl, 3-methyl-2-cyclohexylbutyl, 1-adamantylethyl, 2-adamantylethyl, and adamantylmethyl.

Examples of the straight or branched ($C_6$-$C_{14}$) aryl or ($C_6$-$C_{14}$) aryl-($C_1$-$C_5$) alkyl group are phenyl, 1- or 2-naphthyl, anthracenyl, benzyl, 2-phenylethyl 1-phenylethyl, 3-phenylpropyl, 2-anthracenylpropyl, 1-anthracenylpropyl, naphthylmethyl, 2-naphthylethyl, 1-naphthylethyl, 3-naphthylpropyl, 2-naphthylpropyl, 1-naphthylpropyl, cyclohexylmethyl, 5-phenylpentyl, 3-phenylpentyl, 3-methyl-2-phenylbutyl.

Examples of the straight or branched heterocyclic or heterocyclo-($C_1$-$C_5$) alkyl group are thienyl, quinolyl, pyridyl, N-methylpiperidinyl, 5-tetrazolyl, 2-(4,5-dihydroxazolyl), 1,2,4-oxadiazolidin-3-yl-5-one, purine and pyrimidine bases, e.g. uracyl, optionally substituted as indicated in the general definitions above.

Examples of the ($C_6$-$C_{10}$) aroyl groups are benzoyl and naphthoyl.

Examples of the ($C_6$-$C_{10}$) arylsulphonyl groups are tosyl and benzoylsulphonyl.

What is meant by halogen is fluorine, chlorine, bromine and iodine.

Examples of substituted groups are pentafluorophenyl, 4-phenyl-benzyl, 2,4-difluorobenzyl, 4-aminobutyl, 4-hydroxybutyl, dimethyl-aminoethyl, p-nitrobenzoyl, and p-cyanobenzoyl.

An example of the polyaminoalkyl residue is —$(CH_2)_m$—$NR_{15}$—$(CH_2)_p$—$NR_{16}$—$(CH_2)_q$—$NH_2$, where m, p and q are whole numbers from 2 to 6 inclusive and $R_{15}$ and $R_{16}$ are a straight or branched ($C_1$-$C_6$) alkyl group, for example 4-aminobutyl-2-aminoethyl, 3-aminopropyl-4-aminobutyl, or 3-aminopropyl-4-aminobutyl-3-aminopropyl.

Examples of the glycosyl residue are 6-D-galactosyl and 6-D-glucosyl.

What is meant by amino acid is the generic definition of an organic compound bearing at least one carboxyl residue and at least one amine residue. Examples of amino acid residues are the natural amino acids, in the possible enantiomeric forms; among these, the ones preferred are glycine, alanine, phenylalanine, valine, leucine, isoleucine, aspartic acid, glutamic acid, lysine, arginine, tyrosine, and γ-aminobutyric acid; all the amino acids can be salified, if necessary, on the free carboxyl and/or on the free basic group with pharmaceutically acceptable bases or acids.

Examples of pharmaceutically acceptable salts are, in the case of atoms of nitrogen of a basic nature, salts with pharmaceutically acceptable acids, both inorganic and organic, such as, for example, hydrochloric acid, sulphuric acid, acetic acid, or, in the case of an acid group, such as carboxyl, salts with pharmaceutically acceptable bases, both organic and inorganic, such as, for example, alkaline and alkaline-hearth hydroxides, ammonium hydroxide, and amines, including heterocyclic amines. In the case of Y equal to 4-trimethyl-ammonium-3-hydroxy-butanoyl, pharmaceutically acceptable salts are known and amply described, for example in WO 00/06134.

A first group of preferred compounds comprises formula (I) compounds in which n and m are equal to 1.

A second group of preferred compounds comprises formula (I) compounds in which n and m are both 0.

In the context of the above-mentioned two preferred groups, those preferred are the formula (I) compounds, in which $R_4$ is different from hydrogen, and particularly a straight or branched $C_1$-$C_5$ alkyl or $C_1$-$C_5$ alkenyl group or a $C_3$-$C_{10}$ cycloalkyl group, or a straight or branched ($C_3$-$C_{10}$) cycloalkyl-($C_1$-$C_5$) alkyl group, or a $C_6$-$C_{14}$ aryl group, or a straight or branched ($C_6$-$C_{14}$) aryl-($C_1$-$C_5$) alkyl group, or a straight or branched heterocyclic or heterocyclo-($C_1$-$C_5$) alkyl group, said heterocyclic group containing at least one heteroatom selected from an atom of nitrogen, optionally substituted with a ($C_1$-$C_5$) alkyl group, and/or an atom of oxygen and/or sulphur; said alkyl, alkenyl, cycloalkyl, aryl, aryl-alkyl, heterocyclic or heterocylo-alkyl groups, which may be substituted with one or more groups selected from: halogen, hydroxy, $C_1$-$C_5$ alkyl, $C_1$-$C_5$ alkoxy, phenyl, cyano, nitro, —$NR_6R_7$, where $R_6$ and $R_7$, which may be the same or different, are straight or branched ($C_1$-$C_5$) alkyl; the —COOH group or one of its pharmaceutically acceptable esters; or the —$CONR_8R_9$ group, where $R_8$ and $R_9$, which may be the same or different, are hydrogen, straight or branched ($C_1$-$C_5$) alkyl, according to the definitions outlined above as examples.

One group of particularly preferred compounds includes:

(E)-7-tert-butoxyiminomethyl-20-O-(4-trimethyl-ammonium-3-hydroxy)butanoyl-camptothecin bromide (ST2204);

(E)-7-tert-butoxyiminomethyl-20-O-(4-trimethyl-ammonium)butanoyl-camptothecin bromide (ST2200);

(E)-7-tert-butoxyiminomethyl-20-O-hemisuccinyl-camptothecin;

(E)-7-tert-butoxyiminomethyl-20-O-[2-(dimethylamino)ethylamino]succinyl-camptothecin hydrochloride (ST1657);

20-O-(benzylglycyl)succinyl-camptothecin (ST1451);

20-O-(tert-butylglycyl)succinyl-camptothecin bromide (ST1453);

7-tert-butoxyiminomethyl-20-O-(tert-butylglycyl)succinyl-camptothecin (ST1616);

20-O-(glycyl)succinyl-camptothecin (ST1452);

20-O-(2-methoxyphenylglycyl)succinyl-camptothecin (ST1454);

7-tert-butoxyiminomethyl-20-O-(2-methoxyphenylglycyl)succinyl-camptothecin (ST1617).

The formula (I) compounds can be prepared with the process described here below and exemplified for the preferred compounds of the invention.

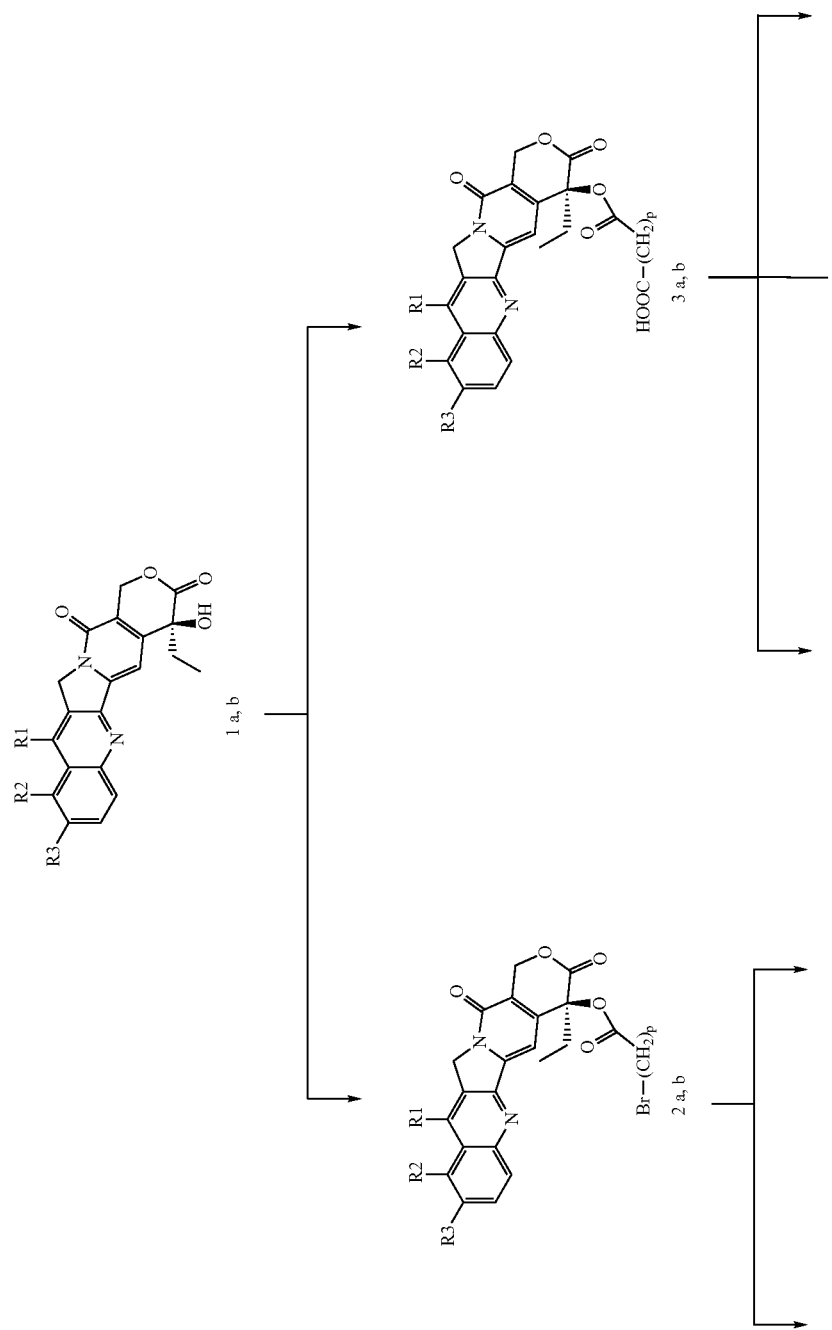

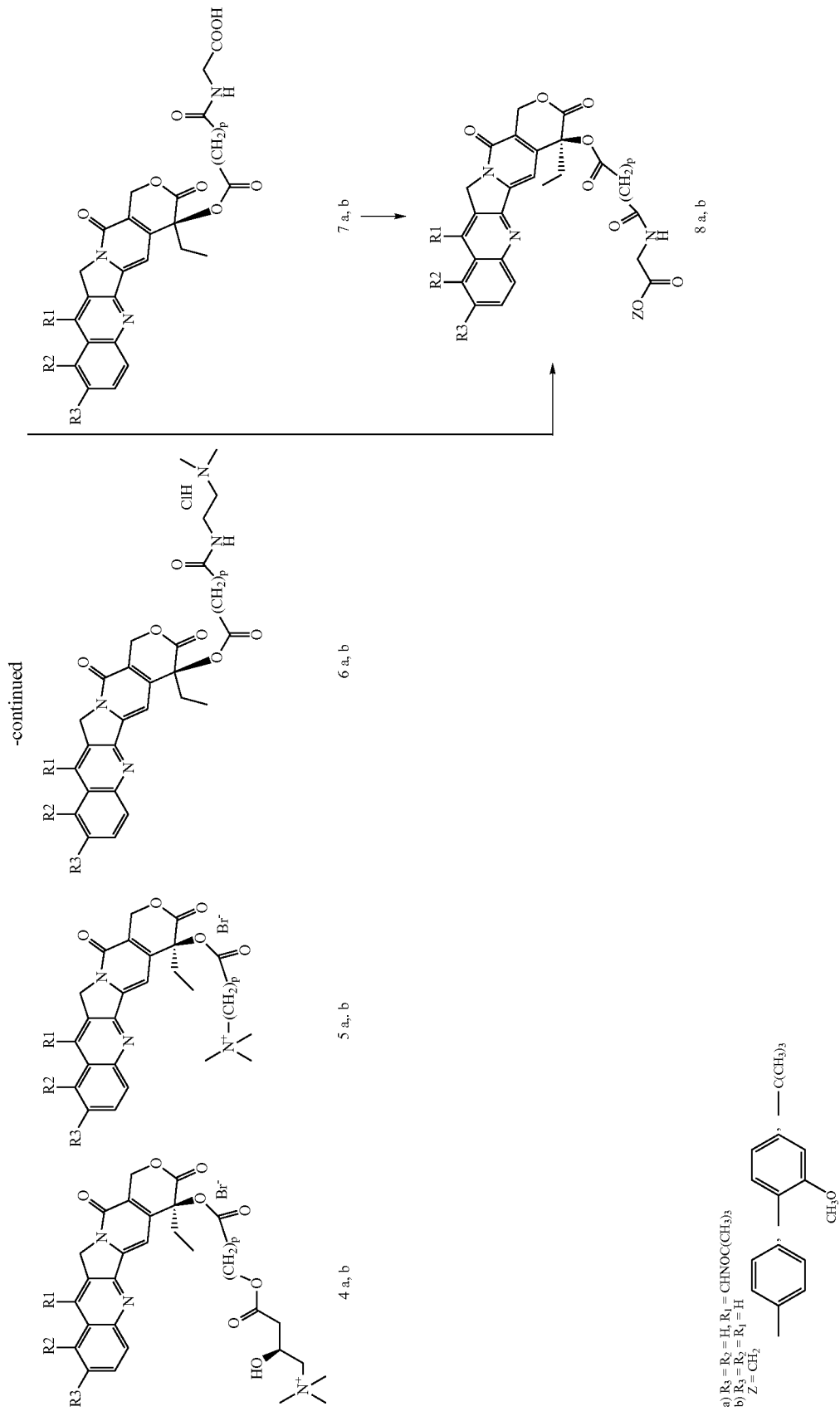

It is quite obvious to the person having ordinary experience in the field that the process scheme applies to all the compounds covered by formula (I), since the method for obtaining the starting compounds is fully described in the above-mentioned patent EP 1044997.

In general terms, the formula (I) compounds, where n and m are 0, are obtained by means of a process comprising:

a) reaction of the camptothecin, optionally substituted with the $R_1$, $R_2$ and $R_3$ groups defined above, with a carboxylic acid bearing a leaving group in ω, to obtain the respective ester in position 20;

b) substitution of the leaving group with the Y group.

In general terms the formula (I) compounds, where n and m are 1, are obtained by a process consisting of:

a) reaction of the camptothecin, optionally substituted with the $R_1$, $R_2$ and $R_3$ groups defined above, with a bicarboxylic acid with 3 to 11 carbon atoms, to obtain the respective hemiester in position 20;

b) transformation of the free carboxyl group of said hemiester to the respective amide —NH—Y.

General Procedure

Preparation of the Intermediate Product 2a,b

The products described in the synthesis scheme are obtained by reaction of camptothecin 1a,b dissolved in a mixture of an aprotic solvent, such as, for example, DMF or halogenated or ether solvents, and in the presence of non-aqueous organic or inorganic bases, such as tertiary amines or $K_2CO_3$ or in the presence of only the base in those cases in which the latter is liquid at the reaction temperature, at a temperature between −10 and +80° C., are added from 2 to 30 equivalents of variously activated carboxylic acids, all bearing a leaving group such as OTs, Cl, Br, or I in ω.

Preparation of the Intermediate Product 3a,b

To a mixture of camptothecin 1a,b dissolved in a mixture of an aprotic solvent such as, for example, DMF or halogenated or ether solvents, and in the presence of non-aqueous organic or inorganic bases, such as tertiary amines or $K_2CO_3$, or in the presence of the base alone in those cases in which the latter is liquid at the reaction temperature, at a temperature between −10 and +80° C., are added from 2 to 30 equivalents of carboxylic acid activated as acyl halogenide or as anhydride or mixed anhydride or imidazolide.

The solvent is removed in vacuo and the product purified by chromatography.

Preparation of the Intermediate Products 4a,b and 5a,b

To the intermediate product 2a,b dissolved in a mixture of an aprotic solvent, such as, for example, DMF or THF or halogenated or ether solvents, and in the presence of non-aqueous organic or inorganic bases such as tertiary amines or $K_2CO_3$, or in the presence of the base alone in those cases in which the latter is liquid at the reaction temperature, at a temperature between +20 and +80° C., are added from 2 to 30 equivalents of suitably substituted alkyl carboxylates or suitably substituted $NR_{12}R_{13}R_{14}$ amines and the reaction continues for time periods ranging from 15 to 36 h.

The solvent is removed in vacuo and the product purified by chromatography or by crystallisation.

Preparation of the Intermediate Product 6a,b

To the intermediate product 3a,b, activated as acyl halogenide or as anhydride or mixed anhydride or imidazolide, dissolved in a mixture of an aprotic solvent, such as, for example, DMF or THF or halogenated or etheral solvents, and in the presence of non-aqueous organic or inorganic bases such as tertiary amines or $K_2CO_3$ or in the presence of the base alone in those cases in which the latter is liquid at the reaction temperature, at a temperature between +20 and +80° C., are added from 2 to 30 equivalents of suitably substituted alkyl amines and the reaction continues for time periods ranging from 15 to 36 h.

The solvent is removed in vacuo and the product purified by chromatography or by crystallisation.

Preparation of the Intermediate Product 7a,b

To the intermediate product 3a,b, activated as acyl halogenide or as anhydride or as mixed anhydride or imidazolide, dissolved in a mixture of an aprotic solvent, such as, for example, DMF or THF or halogenated or ether solvents, and in the presence of non-aqueous organic or inorganic bases, such as tertiary amines or $K_2CO_3$, or in the presence of the base alone in those cases in which the latter is liquid at the reaction temperature, at a temperature between +20 and +80° C., are added from 2 to 30 equivalents of amino acids and the reaction continues for time periods ranging from 15 to 36 h. The solvent is removed in vacuo and the product purified by chromatography or by crystallisation.

Preparation of 8a,b

The intermediate product 7a,b is dissolved in an aprotic solvent such as, for example, DMF, halogenated solvents or ether solvents. To the solution thus obtained are added from 2 to 20 equivalents of an aliphatic or aromatic alcohol, from 2 to 10 equivalents of base and an excess from 2 to 10 equivalents of condensing agent such as, for example, DCC, or EDC. The reaction is held at a temperature ranging from 25 to 50° C. for a time period ranging from 4 to 24 h. The product is purified by chromatography. The product 8a,b is also obtained directly from 3a,b using an esterified amino acid.

Pharmaceutically acceptable salts are obtained with conventional methods reported in the literature and do not require any further description.

The compounds described in the present invention are topoisomerase I inhibitors and therefore are useful as medicaments, particularly for the treatment of diseases that benefit from the inhibition of said topoisomerase. In particular, the compounds according to the present invention display antiproliferative activity and are therefore used on account of their therapeutic activity and possess physicochemical properties that make them suitable for formulation in pharmaceutical compositions.

The pharmaceutical compositions contain at least one formula (I) compound as an active ingredient, in an amount such as to produce a significant therapeutic effect. The compositions covered by the present invention are wholly conventional and are obtained with methods which are common practice in the pharmaceutical industry. According to the administration route opted for, the compositions will be in solid or liquid form, suitable for the oral, parenteral, or intravenous administration. The compositions according to the present invention contain, along with the active ingredient, at least one pharmaceutically acceptable vehicle or excipient. Particularly useful may be formulation coadjuvants, such as, for example, solubilisers, dispersant agents, suspension agents and emulsifiers. Aqueous compositions are indicated.

The formula (I) compounds can also be used in combination with other active ingredients, such as, for example, other anticancer drugs or other drugs with antiparasitic or antiviral activity, both in separate and in single dosage forms.

The compounds according to the present invention are useful as medicaments with anticancer activity, for example, in lung cancers, such as non-microcytoma lung cancer, or in colorectal or prostate tumours or gliomas.

The cytotoxic activity of the compounds according to the present invention has been assayed in cell systems of human tumour cells, using the antiproliferative activity test as the method of evaluating the cytotoxic potential.

The cell line used is a non-microcytoma pulmonary adenocarcinoma called NCI H460, belonging to the NSCLC (non small cell lung cancer) class.

Anticancer Activity

To evaluate the effect of the compounds according to the present invention, their cytotoxocity against the non-microcytoma lung cancer cell line (NCI-H460) was evaluated. Cells from the American Type Culture Collection (ATCC) were maintained in culture in RPMI 1640 (GIBCO) containing 10% foetal calf serum and gentamicin sulphate at a concentration of 50 µg/ml.

The cells were seeded in a volume of 250 µl in 96-well plates and incubated for 24 h at 37° C. The next day, the study compounds were added at scalar concentrations from 1 µM to 0.004 µM, and the cells were incubated for another 2 h at 37° C. in a humidified atmosphere containing 5% $CO_2$. The cells were washed 3 times, overturning the plates each time and adding PBS. 200 µl/well of RPMI 1640 medium containing 10% FCS were added and the plates were incubated at 37° C. for a further 72 h. On day 5, the growth medium was removed by overturning the plates, and 200 µl/well of PBS and 50 µl of 80% cold TCA were added. The plates were then incubated in ice for at least 1 h. The TCA was removed by overturning; the plates were washed 3 times by immersion in distilled water and dried first on blotting paper and then under a hot air jet. 200 µl of 0.4% sulforodamine B in 1% acetic acid were added to all wells. The plates were incubated at room temperature for a further 30 minutes. The sulforodamine B was removed by overturning; the plates were washed by immersion 3 times in 1% acetic acid and then dried first on blotting paper and then with a jet of hot air. 200 µl of Tris base 10 mM were added to all wells and the plates were subjected to stirring for at least 20 minutes. The optical density was measured using a Multiskan spectrophotometer at 540 nm.

Table 1 presents the $IC_{50}$ values, that is to say the concentration capable of inhibiting 50% of cell survival, for each compound examined, processed using ALLFIT software.

TABLE 1

| Product | NCI-H460 $IC_{50}$ (µM) |
| --- | --- |
| ST1451 | 0.15 |
| ST1452 | 1.6 |
| ST1453 | 0.26 |
| ST1454 | 0.16 |
| ST1616 | 0.004 |
| ST1617 | 0.029 |
| ST1657 | 0.012 |
| ST2200 | 0.017 |
| ST2204 | 0.041 |

The following examples further illustrate the invention, with reference to the scheme outlined above

EXAMPLE 1

(E)-7-tert-butoxyiminomethyl-20-O-(4-bromo)-butyryl-camptothecin (2a) (ST2599)

In a flask, kept sheltered from the light, were loaded 2 g (4.5 mmol) of 7-tert-butoxyiminomethyl-camptothecin (1a) and 25 mL of pyridine; the mixture was cooled in an ice bath and 4.5 mL (38.9 mmol, 8.6 eq.) of 4-bromobutyryl chloride were added dropwise. After 3 h the reaction mixture was brought to dryness and then purified by flash chromatography on a column ($CH_2Cl_2$/acetone 98:2) to obtain 1.26 g (2.1 mmol, 46.7%) of product ($T_{dec}$=212° C.).

$R_f$=0.61 ($CH_2Cl_2$/dioxane 95:5). MS (IS): $[MH]^+$=596.2, 598.2; $[M+Na]^+$=618.2, 620.2; $[M-1]^-$=594.0, 596.0 Elemental analysis: Calculated: C, 58.29; H, 5.19; N, 7.04. Found: C, 58.25; H, 5.18; N, 7.03. $^1H$ NMR (300 MHz, DMSO, δ): 0.95-1.00 (t, 3H, $CH_3$), 1.50 (s, 9H, tBu), 1.95-2.20 (m, 4H, 2×$CH_2$), 2.65-2.75 (t, 2H, $CH_2$), 3.50-3.60 (t, 2H, $CH_2$), 5.30 (s, 2H, $CH_2$), 5.50 (s, 2H, $CH_2$), 7.10 (s, 1H, CH), 7.65-7.75 (t, 1H, CH), 7.85-7.95 (t, 1H, CH), 8.10-8.20 (d, 1H, CH), 8.50-8.60 (d, 1H, CH), 9.20 (s, 1H, CH). $^{13}C$ NMR (75.4 MHz, DMSO, δ): 8.1; 28.4; 28.2; 28.1; 31.0; 31.5; 33.8; 34.2; 45.9; 53.6; 65.4; 77.8; 82.1; 96.4; 120.4; 125.8, 126.5; 129.8; 130.4; 131.2; 133.0; 144.5; 146.3; 147.7; 149.4; 153.8; 157.0; 168.0; 172.5.

Cytotoxicity test on H460 cells: $IC_{50}$=42 nM±6

EXAMPLE 2

(E)-7-tert-butoxyiminomethyl-20-O-(4-trimethyl-ammonium-3-hydroxy)butanoyl-camptothecin bromide (4a) (ST2204)

To a solution of 510 mg (0.86 mmol) of (E)-7-tert-butoxy-iminomethyl-20-O-(4-bromo)-butyryl-camptothecin (2a) in 10 mL of anhydrous DMF were added 906 mg (5.6 mmol, 6.5 eq.) of L-carnitine inner salt. The mixture thus obtained was stirred at room temperature and sheltered from the light. After 16 h the reaction showed 40% conversion and 600 mg (3.7 mmol, 4.3 eq.) of L-carnitine inner salt were then added. After another 20 h the excess carnitine was eliminated after diluting the mixture with 15 mL of $CH_2Cl_2$, with an aqueous washing (4 mL). The resulting organic phase was shaken with 10 mL of $H_2O$ to extract the product and eliminate the lipophilic impurities in $CH_2Cl_2$. 161 mg (0.21 mmol, 24%) of a yellow solid were obtained ($T_{dec.}$=189° C.).

$R_f$=0.38 ($CH_2Cl_2$/$CH_3OH$ 7:3). MS (IS): $M^+$=677.4 Elemental analysis: Calculated: C, 57.02; H, 5.93; N, 7.39. Found: C, 56.98; H, 5.92; N, 7.38. (2% $H_2O$). $^1H$ NMR (300 MHz, DMSO, δ): 0.90-1.00 (t, 3H, $CH_3$), 1.50 (s, 9H, tBu), 1.80-1.95 (quintet, 2H, $CH_2$), 2.10-2.20 (q, 2H, $CH_2$), 2.60-2.70 (t, 2H, $CH_2$), 3.10 (s, 9H, $NMe_3$), 3.20-3.40 (t, 4H, 2×$CH_2$), 4.05-4.15 (t, 2H, $CH_2$), 4.35-4.45 (m, 1H, CH), 5.30 (s, 2H, $CH_2$), 5.50 (s, 2H, $CH_2$), 7.10 (s, 1H, CH), 7.70-7.80 (t, 1H, CH), 7.85-7.95 (t, 1H, CH), 8.15-8.20 (d, 1H, CH), 8.55-8.65 (d, 1H, CH), 9.30 (s, 1H, CH). $^{13}C$ NMR (75.4 MHz, DMSO, δ): 8.2; 24.4; 28.0; 28.2; 30.5; 31.0; 53.3; 54.1; 62.9; 63.7; 67.0; 69.9; 76.6; 81.3; 95.3; 119.7, 125.0; 125.8; 127.3; 129.0; 130.4; 131.2; 132.6; 144.3; 146.0; 146.0; 149.4; 153.0; 157.1; 168.0; 170.7; 172.3.

EXAMPLE 3

(E)-7-tert-butoxyiminomethyl-20-O-(4-trimethylammonium)-butanoyl-camptothecin bromide (5a) (ST2200)

In a solution of 500 mg (0.84 mmol) of (E)-7-tert-butoxy-iminomethyl-20-O-(4-bromo)-butyl-yl-camptothecin (2a) in 10 mL of THF, gaseous trimethylamine was bubbled for 15 h at room temperature and sheltered from the light. The THF was then removed by evaporation and the product was purified by re-precipitation with ethyl ether from a methanol solution. 300 mg (0.46 mmol, 54.7%) of product were obtained as a yellow solid ($T_{dec}$=212° C.).

$R_f$=0.38 ($CH_2Cl_2$/$CH_3OH$ 7:3). MS (IS): $M^+$=575.4. Elemental analysis: Calculated: C, 58.57; H, 5.95; N, 8.54.

Found: C, 58.53; H, 5.94; N, 8.53. (1% $H_2O$). $^1$H NMR (300 MHz, DMSO, δ): 0.95-1.00 (t, 3H, $CH_3$), 1.50 (s, 9H, tBu), 1.90-2.00 (m, 2H, $CH_2$), 2.15-2.25 (q, 2H, $CH_2$), 2.60-2.80 (m, 2H, $CH_2$), 3.00 (s, 9H, $NMe_3$), 3.25 (m, 2H, $CH_2$), 5.40 (s, 2H, $CH_2$), 5.50-6.00 (d, 2H, $CH_2$), 7.10 (s, 1H, CH), 7.70-7.80 (t, 1H, CH), 7.85-7.95 (t, 1H, CH), 8.10-8.20 (d, 1H, CH), 8.55-8.65 (d, 1H, CH), 9.30 (s, 1H, CH). $^{13}$C NMR (75.4 MHz, DMSO, δ): 8.1; 18.4; 28.6; 20.2; 21.3; 53.6; 54.8; 65.4; 67.2; 77.3; 79.0; 82.1; 96.5; 120.2, 125.8; 126.0; 128.0; 129.5; 130.1; 133.2; 144.2; 146.1; 147.0; 149.5; 153.0; 157.9; 168.0; 172.9.

EXAMPLE 4

(E)-7-tert-butoxyiminomethyl-20-O-hemisuccinyl-camptothecin (3a)

In a flask kept sheltered from the light were dissolved 6 g (13.4 mmol) of 7-tert-butoxyiminomethyl-camptothecin (1a), 26.82 g (268 mmol) of succinic anhydride and 600 mg (4.9 mol) of 4-dimethylaminopyridine in 60 mL of anhydrous pyridine; the mixture thus obtained was stirred at T=60° C. After 22 h the solvent was removed by evaporation and the residue extracted with $CH_2Cl_2$. The organic phase was shaken with HCl 0.5% (2×20 mL) and dried on anhydrous $Na_2SO_4$.

The crude reaction product was purified by chromatography on silica gel with $CH_2Cl_2/CH_3OH$ 95:5→9:1 to obtain 5.3 g (9.7 mmol, 72.4%) of product.

MS (IS): $[M+H]^+$=548.3. Elemental analysis: Calculated: C, 63.62; H, 5.30; N, 7.68. Found: C, 63.59; H, 5.29; N, 7.67. $^1$H NMR (300 MHz, $CDCl_3$, δ): 0.95-1.05 (t, 3H, $CH_3$), 1.50 (s, 9H, tBu), 2.10-2.30 (m, 4H, $2×CH_2$), 2.90-3.10 (m, 2H, $CH_2$), 5.35-5.45 (d, 2H, $CH_2$), 5.70-5.80 (d, 2H, $CH_2$), 7.40 (s, 1H, CH), 7.65-7.75 (d, 2H, 2×CH), 8.10-8.20 (d, 2H, 2×CH), 8.90 (s, 1H, CH). $^{13}$C NMR (75.4 MHz, DMSO, δ): 8.1; 28.0; 30.2; 32.0; 52.1; 67.0; 82.4; 120.6, 122.1; 124.7; 125.5; 128.2; 129.1; 142.7; 144.0; 146.4; 147.3; 151.5; 156.8; 172.9; 174.4. $^{13}$C NMR (75.4 MHz, $CDCl_3$, δ): 8.1; 28.0; 30.2; 32.0; 52.1; 67.0; 82.4; 120.6, 122.1; 124.7; 125.5; 128.2; 129.1; 142.7; 144.0; 146.4; 147.3; 151.5; 156.8; 167.2; 172.9; 174.4.

EXAMPLE 5

(E)-7-tert-butoxyiminomethyl-20-O-[2-(dimethylamino)ethylamino]succinyl-camptothecin hydrochloride (6a) (ST1657)

The intermediate product 3a (3 g, 5.48 mmol) was dissolved in 60 ml of anhydrous $CH_2Cl_2$ (60 ml). To the solution, cooled in an ice bath, were added 22 ml of oxalyl chloride. On completing the addition, the cooling bath was removed and the reaction was left at room temperature for 8 h. After this, the reaction was processed by removing the solvent and excess oxalyl chloride and then by washing, repeatedly adding and evaporating the anhydrous $CH_2Cl_2$. (Any oxalic acid remaining is decomposed).

The crude reaction product (a red solid) (3.1 g) was used as is in the next reaction without any further purification.

In a flask fitted with a drip funnel were dissolved 3.4 g (6 mmol) of the crude acid chloride described previously in 80 ml of anhydrous $CH_2Cl_2$. To the resulting solution, held at 0° C., was added dropwise a solution of 1 ml of N,N-dimethylethylenediamine and 1.25 ml of TEA in 10 ml of $CH_2Cl_2$. Two hours after the addition, the reaction was checked. The reaction was processed by adding a further aliquot of $CH_2Cl_2$ and then shaking it with several portions of water. The resulting organic phase was dried on anhydrous $Na_2SO_4$ and concentrated, obtaining 4.6 g of a red solid which was then purified. To the solid redissolved in $CH_2Cl_2$ was added gaseous HCl dissolved in THF. After a 10-minute stirring the solution was concentrated on the Rotavapor until all the solvent and excess hydrochloric acid was removed. The crude reaction product was dissolved in a minimal quantity of $CH_2Cl_2$ and filtered to remove any dispersed solid.

ST1657 was precipitated from the solution by adding acetone (1.5 g of crude product yielded 1 g of precipitated solid). The total yield of ST1657 from 3a was 25%.

$R_f$=0.2 ($CH_2Cl_2/CH_3OH$ 8:2). $T_{dec}$=230° C. MS (IS): $[M_{ion}]^+$=618. Elemental analysis: Calculated: C, 60.60; H, 6.12; N, 10.71. Found: C, 60.56; H, 6.11; N, 10.70. (2% $H_2O$). $^1$H NMR (300 MHz, DMSO, δ): 0.90-1.00 (t, 3H, CH3), 1.50 (s, 9H, tBu), 2.05-2.20 (q, 2H, $CH_2$), 2.40-2.50 (q, 2H, $CH_2$), 2.60-2.70 (s, 6H, $2×CH_3$), 2.70-2.90 (m, 4H, $2×CH_2$), 3.00-3.10 (q, 2H, $CH_2$), 5.30 (s, 2H, $CH_2$), 5.50 (s, 2H, $CH_2$), 7.10 (s, 1H, CH), 7.70-7.80 (t, 1H, CH), 7.85-7.95 (t, 1H, CH), 8.15-8.20 (d, 1H, CH), 8.20-8.30 (t, 1H, NH), 8.55-8.60 (d, 1H, CH), 9.30 (s, 1H, CH). $^{13}$C NMR (75.4 MHz, DMSO, δ): 8.3; 27.9; 29.4; 30.4; 31.0; 34.6; 42.9; 53.2; 56.6; 66.9; 71.0; 76.6; 81.3; 95; 7; 119.6; 124.9; 125.7; 127.7; 128.9; 130.4; 131.2; 132.5; 144.3; 146.4; 149.4; 153.1; 157.0; 168.0; 171.8; 172.2.

EXAMPLE 6

20-O-(benzylglycyl)succinyl-camptothecin (7b) (ST1451)

500 mg (1.44 mmol) of camptothecin (1b), 4 g (40 mmol; 28 eq.) of succinic anhydride and dimethylaminopyridine in a catalytic amount were suspended in 5 ml of pyridine; the mixture was stirred at 50° C. for 48 h. On completion of the reaction, 50 mL of HCl 6N were added and the solid thus obtained was recrystallised by MeOH to yield 452 mg (1 mmol; 70%) of a product with $R_f$=0.2 in $CH_2Cl_2$/MeOH 95:5.

To a suspension of 1 mmol of the acid thus obtained in 10 mL of anhydrous $CH_2Cl_2$, cooled to T=0° C., were added 1.27 g (10 mmol; 10 eq.) of oxalyl chloride. The mixture was left to stir for 3 h until complete formation of the acid chloride was achieved; after bringing the reaction product to dryness, extraction was done with 10 mL of anhydrous $CH_2Cl_2$ and 1.65 g (10 mmol; 10 eq.) of glycine-benzyl-ester and 1.5 mL (15 mmol; 15 eq.) of triethylamine were added. After 3 h the mixture was brought to dryness, the residue was extracted with $CH_2Cl_2$ and the organic phase thus obtained was washed with HCl 1N and then with $H_2O$. The crude product thus obtained was purified by chromatography on an $SiO_2$ column with $CH_2Cl_2$/MeOH 95:5 to obtain 400 mg (0.67 mmol; 67%) of the desired product. $R_f$=0.38 in $CH_2Cl_2$ 92:8.

M.P.=189° C. $α_D$=−5.2° (c=0.44 in $CHCl_3$/MeOH 8:2). MS (IS): $[M+1]^+$=597. Elemental analysis: Calculated: C, 66.55; H, 4.87; N, 7.06. Found: C, 66.52; H, 4.86; N, 7.05. $^1$H NMR (300 MHz, DMSO, δ): 0.95-1.00 (t, 3H, $CH_3$), 2.10-2.20 (q, 2H, $CH_2$), 2.40-2.60 (m, 2H, $CH_2$), 2.65-2.85 (m, 2H, $CH_2$), 3.90-4.10 (m, 2H, $CH_2$), 5.00 (s, 2H, $CH_2$), 5.30 (s, 2H, $CH_2$), 5.50 (s, 2H, $CH_2$), 7.10 (s, 1H, CH), 7.25-7.35 (m, 5H, Ph), 7.65-7.80 (m, 2H, 2CH), 8.10-8.20 (q, 2H, 2CH), 8.40-8.50 (t, 1H, NH), 8.70 (s, 1H, CH). $^{13}$C NMR (75.4 MHz, DMSO, δ): 7.5; 28.8; 29.4; 30.2; 40.6; 40.7; 50.0; 65.7; 66.1; 75.8; 95;3; 118.6; 127.5; 127.7; 127.8; 127.9; 128.2; 128.4;

128.9; 129.6; 130.2; 131.4; 135.7; 145.4; 145.7; 147.8; 152.3; 156.4; 167.1; 169.7; 170.9; 171.1.

EXAMPLE 7

20-O-(terbutylglycyl)succinyl-camptothecin bromide (8b) (ST1453)

500 mg (1.44 mmol) of camptothecin (1b), 4 g (40 mmol; 28 eq.) of succinic anhydride and dimethylaminopyridine in a catalytic amount were suspended in 5 ml of pyridine; the mixture was stirred at 50° C. for 48 h. On completion of the reaction, 50 mL of HCl 6N were added and the solid thus obtained was recrystallised by MeOH to yield 452 mg (1 mmol; 70%) of a product with $R_f$=0.2 in $CH_2Cl_2$/MeOH 95:5.

To a suspension of 1 mmol of the acid thus obtained in 10 mL of anhydrous $CH_2Cl_2$, cooled to T=0° C., were added 1.27 g (10 mmol; 10 eq.) of oxalyl chloride. The mixture was left to stir for 3 h until complete formation of the acid chloride was achieved; after bringing the reaction product to dryness, extraction was done with 10 mL of anhydrous $CH_2Cl_2$ and 1.31 g (10 mmol; 10 eq.) of glycine-tert-butyl-ester and 1.5 mL (15 mmol; 15 eq.) of triethylamine were added. After 3 h the mixture was brought to dryness, the residue was extracted with $CH_2Cl_2$ and the organic phase thus obtained was washed with HCl 1N and then with $H_2O$. The crude product thus obtained was purified by chromatography on an $SiO_2$ column with $CH_2Cl_2$/MeOH 95:5 to yield 390 mg (0.7 mmol; 70%) of the desired product. $R_f$=0.4 in $CH_2Cl_2$ 92:8.

$T_{dec}$=213° C. $\alpha_D$=-52.1° (c=0.41 in $CHCl_3$/MeOH 8:2). MS (IS): $[M+1]^+$=562; $M+Na^+$=584; $[M-1]^-$=560. Elemental analysis: Calculated: C, 64.17; H, 5.53; N, 7.49. Found: C, 64.12; H, 5.51; N, 7.46. $^1$H NMR (300 MHz, DMSO, δ): 0.90-1.00 (t, 3H, $CH_3$), 1.40 (s, 9H, tBU), 2.10-2.20 (q, 2H, $CH_2$), 2.35-2.55 (m, 2H, $CH_2$), 2.60-2.85 (m, 2H, $CH_2$), 3.75-4.00 (m, 2H, $CH_2$), 5.30 (s, 2H, $CH_2$), 5.50 (s, 2H, $CH_2$), 7.20 (s, 1H, CH), 7.70-7.80 (t, 1H, CH), 7.85-7.95 (t, 1H, CH), 8.10-8.15 (d, 1H, CH), 8.20-8.25 (d, 1H, CH), 8.30-8.35 (t, 1H, NH), 8.70 (s, 1H, CH). $^{13}$C NMR (75.4 MHz, DMSO, δ): 7.5; 27.5; 28.9; 29.4; 30.2; 40.3; 41.2; 50.0; 66.1; 75.8; 80.4; 95; 4; 118.6; 127.6; 127.9; 128.4; 128.9; 129.7; 130.2; 131.4; 145.4; 145.7; 147.8; 152.3; 156.5; 167.1; 169.0; 170.7; 171.2.

EXAMPLE 8

7-ter-butoxyiminomethyl-20-O-(terbutylglycyl)succinyl-camptothecin (8a) (ST1616)

387 mg (0.71 mmol) of 3a were dissolved in 100 mL of anhydrous $CH_2Cl_2$. The solution was cooled in an ice bath, and 3 mL of oxalyl chloride were then added. On completion of the addition, the ice bath was removed and the reaction was left at room temperature for 6 h. On completion of the reaction, the mixture was brought to dryness and washed several times with $CH_2Cl_2$. To the acid chloride thus obtained was added a solution of glycine tert-butyl ester in $CH_2Cl_2$, obtained by releasing with NaOH 2N 1.6 g (9.6 mmol; 13 eq. compared to the starting 3a) of the corresponding hydrochloride, and 1.6 mL of triethylamine. After 3 h the reaction mixture was diluted with $CH_2Cl_2$ and washed with HCl 1N, NaOH 2N and with $NaCl_{sat}$. The organic phase was then dried on anhydrous sodium sulphate and purified on a preparative column ($CH_2Cl_2$/MeOH 9:1) to yield 360 mg (0.54 mmol; 76%) of end product.

$R_f$=0.47 in $CH_2Cl_2$/MeOH 95:5. M.P.=190° C. $[M-1]^-$=659. Elemental analysis: Calculated: C, 63.64; H, 6.06; N, 8.48. Found: C, 63.67; H, 6.09; N, 8.51. $^1$H NMR (300 MHz, DMSO, δ): 0.95-1.00 (t, 3H, $CH_3$), 1.40 (s, 9H, tBu), 1.50 (s, 9H, tBu), 2.10-2.30 (q, 2H, $CH_2$), 2.40-2.60 (m, 2H, $CH_2$), 2.70-2.90 (m, 2H, $CH_2$), 3.70-4.00 (m, 2H, $CH_2$), 5.40 (s, 2H, $CH_2$), 5.50 (s, 2H, $CH_2$), 7.20 (s, 1H, CH), 7.70-7.80 (t, 1H, CH), 7.90-8.00 (t, 1H, CH), 8.20-8.25 (d, 1H, CH), 8.30-8.40 (t, 1H, NH), 8.60-8.65 (d, 1H, CH), 9.30 (s, 1H, CH). $^{13}$C NMR (75.4 MHz, DMSO, δ): 8.3; 28.0; 28.3; 29.6; 30.1; 31.0; 42.0; 53.1; 66.9; 76.6; 81.2; 81; 3; 96.0; 119.5; 124.9; 125.7; 127.2; 128.9; 130.5; 131.0; 132.4; 144.3; 146.1; 146.2; 149.4; 153.1; 157.0; 167.9; 171.5; 171.2.

EXAMPLE 9

20-O-(glycyl)succinyl-camptothecin (7b) (ST1452)

200 mg (0.34 mmol) of ST1451 were dissolved in 3 mL of a mixture of DMF/EtOH 1:1; the solution was added with Pd-$BaSO_4$ cat. and subjected to hydrogenation at 60 psi. After 1 h the reaction was complete, with formation of a product with Rf=0.2 in $CH_2Cl_2$/MeOH 8:2. The product was purified on an $SiO_2$ column with $CH_2Cl_2$/MeOH 7:3 to yield 157 mg (0.31 mmol; 90%) of the expected product.

$T_{dec}$=255° C. $\alpha_D$=-62° (c=0.4 in $CHCl_3$/MeOH 8:2) MS (IS): $[M-1]^-$=504. Elemental analysis: Calculated: C, 61.78; H, 4.87; N, 7.06. Found: C, 61.74; H, 4.82; N, 7.10. $^1$H NMR (300 MHz, DMSO, δ): 0.90-1.00 (t, 3H, $CH_3$), 2.10-2.20 (q, 2H, $CH_2$), 2.35-2.55 (m, 2H, $CH_2$), 2.65-2.85 (m, 2H, $CH_2$), 3.75-3.90 (m, 2H, $CH_2$), 5.30 (s, 2H, $CH_2$), 5.50 (s, 2H, $CH_2$), 7.20 (s, 1H, CH), 7.70-7.80 (t, 1H, CH), 7.85-7.95 (t, 1H, CH), 8.10-8.15 (d, 1H, CH), 8.20-8.25 (d, 1H, CH), 8.25-8.30 (t, 1H, NH), 8.70 (s, 1H, CH). $^{13}$C NMR (75.4 MHz, DMSO, δ): 8.5; 29.9; 30.4; 31.3; 51.1; 67.2; 76.8; 96.3; 119.7; 128.6; 128.9; 129.4; 130.0; 130.7; 131.2; 132.4; 146.8; 149.9; 153.3; 157.7; 168.1; 171.6; 172.2.

EXAMPLE 10

20-O-(2-methoxyphenylglycyl)succinyl-camptothecin (8b) (ST 1454)

To 55 mg of (7b) ST1452 dissolved in 3 mL of $CH_2Cl_2$, were added 27 mg (0.22 mmol; 1.8 eq.) of dimethylaminopyridine, 150 mg (1.2 mmol; 10 eq.) of guaiacol and 150 mg (0.73 mmol; 7 eq.) of DCC. The mixture was stirred at room temperature overnight. The reaction was diluted with 10 ml of $CH_2Cl_2$, washed with HCl 1N and dried on $Na_2SO_4$. The crude product was purified on a preparative column with $CH_2Cl_2$/MeOH 98/2. 49 mg of product (0.08 mmol; 67%) were obtained.

$T_f$=180° C. $\alpha_D$=-41.1° (c=0.41 in $CHCl_3$/MeOH 8:2). MS (IS): $[M+1]^+$=612; $M+Na^+$=634; $M+K^+$=650. Elemental analysis: Calculated: C, 64.81; H, 4.75; N, 6.87. Found: C, 64.87; H, 4.79; N, 6.83. $^1$H NMR (300 MHz, DMSO, δ): 0.90-1.00 (t, 3H, $CH_3$), 2.10-2.20 (q, 2H, $CH_2$), 2.40-2.60 (m, 2H, $CH_2$), 2.65-2.85 (m, 2H, $CH_2$), 3.70 (s, 3H, $CH_3$), 4.10-4.30 (m, 2H, $CH_2$), 5.30 (s, 2H, $CH_2$), 5.50 (s, 2H, $CH_2$), 6.85-7.00 (m, 2H, 2x$CH_{ar}$), 7.05-7.25 (m, 3H, 2x$CH_{ar}$+$CH_{olef}$), 7.60-7.70 (t, 1H, CH), 7.75-7.85 (t, 1H, CH), 8.05-8.10 (d, 1H, CH), 8.20-8.25 (d, 1H, CH), 8.45-8.55 (t, 1H, NH), 8.70 (s, 1H, CH). $^{13}$C NMR (75.4 MHz, DMSO, δ): 8.5; 25.4; 26.3; 29.8; 30.4; 31.2; 34.3; 48.4; 51.1; 52.7; 67.2; 76.8; 96.3; 113.9; 119.7; 121.5; 123.5; 127.9; 128.6; 128.9; 129.4; 130.0; 130.7; 131.2; 132.4; 146.4; 146.8; 148.9; 151.7; 153.4; 157.5; 169.3; 171.9; 172.2.

EXAMPLE 11

7-ter-butoxyiminomethyl-20-O-(2-methoxy-phenyl-glycyl)succinyl-camptothecin (8a) (ST1617)

180 mg (0.27 mmol) of ST1616 were dissolved in 3 mL of anhydrous $CH_2Cl_2$, and 1.5 mL of trifluoroacetic acid were added to the solution. After 3 h at room temperature the reaction was complete and the mixture was brought to dryness and the residue thus obtained washed several times to eliminate the excess trifluoroacetic acid.

The product was then dissolved in 6 mL of anhydrous $CH_2Cl_2$, and 0.82 mL (7.5 mmol; 28 eq.) of guaiacol, 80 mg (0.65 mmol; 2.4 eq.) of dimethylaminopyridine and 410 mg (2 mmol; 7.4 eq.) of DCC were added to the solution. After 24 h the reaction mixture was filtered through celite and the crude product was purified by chromatography on an $SiO_2$ column with $CH_2Cl_2$/MeOH 92:8 to yield 85 mg (0.12 mmol; 44%) of yellow solid. Rf=0.24 in $CH_2Cl_2$/MeOH 95:5.

$T_{dec}$=170° C. $[M+1]^+$=711; $M+Na^+$=733; Elemental analysis: Calculated: C, 64.23; H, 5.35; N, 7.89. Found: C, 64.29; H, 5.39, 7.84. $^1$H NMR (300 MHz, DMSO, δ): 0.95-1.00 (t, 3H, $CH_3$), 1.50 (s, 9H, tBu), 2.10-2.30 (q, 2H, $CH_2$), 2.40-2.65 (m, 2H, $CH_2$), 2.70-2.95 (m, 2H, $CH_2$), 3.80 (s, 3H, $CH_3$), 4.15-4.35 (m, 2H, $CH_2$), 5.40 (s, 2H, $CH_2$), 5.60 (s, 2H, $CH_2$), 6.90-7.05 (m, 2H, 2×CH), 7.10-7.30 (m, 3H, 2×$CH_{ar}$+$CH_{olef}$), 7.75-7.80 (t, 1H, CH), 7.85-7.90 (t, 1H, CH), 8.30-8.35 (d, 1H, CH), 8.55-8.70 (m, 2H, CH+NH), 9.30 (s, 1H, CH). $^{13}$C NMR (75.4 MHz, DMSO, δ): 8.3; 25.1; 26.0; 27.0; 28.7; 29.6; 30.1; 31.0; 34.0; 48.2; 56.4; 76.6; 81.3; 96.0; 113.6; 119.5; 121.2; 123.3; 124.9; 125.7; 127.2; 127.7; 128.9; 130.5; 131.0; 132.4; 144.3; 146.2; 149.4; 151.4; 157.0; 157.3; 167.9; 169.0; 171.7; 172.0.

The invention claimed is:

1. A compound of Formula I

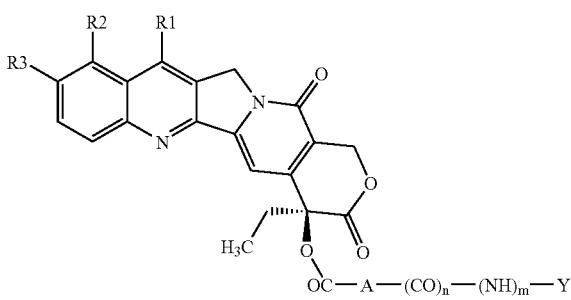

(I)

where:

A is saturated or unsaturated straight or branched $C_1$-$C_8$ alkyl, $C_3$-$C_{10}$ cycloalkyl, straight or branched $C_3$-$C_{10}$ cycloalkyl-$C_1$-$C_8$ alkyl;

n and m are both 1;

Y is BCOOX, where B is a residue of an amino acid, X is H, straight or branched $C_1$-$C_4$ alkyl, benzyl or phenyl, substituted in the available positions with at least one group selected from $C_1$-$C_4$ alkoxy, halogen, nitro, amino, $C_1$-$C_4$ alkyl, $R_1$ is a hydrogen or a —C($R_5$)=N—O—$R_4$ group, in which $R_4$ is hydrogen or a straight or branched $C_1$-$C_5$ alkyl or $C_1$-$C_5$ alkenyl group, or a $C_3$-$C_{10}$ cycloalkyl group, or a straight or branched ($C_3C_{10}$) cycloalkyl-($C_1$-$C_5$) alkyl group, or a $C_6$-$C_{14}$ aryl group, or a straight or branched ($C_6$-$C_{14}$) aryl-($C_1$-$C_5$) alkyl group, or a heterocyclic group or a straight or branched heterocyclic-($C_1$-$C_5$) alkyl group, said heterocyclic group containing at least one heteroatom selected from an atom of nitrogen, optionally substituted with a ($C_1$-$C_5$) alkyl group, and/or an atom of oxygen and/or of sulphur; said alkyl, alkenyl, cycloalkyl, cycloalkylalkyl, aryl, aryl-alkyl, heterocyclic or heterocyclo-alkyl groups may optionally be substituted with one or more groups selected from: halogen, hydroxy, $C_1$-$C_5$ alkyl, $C_1$-$C_5$ alkoxy, phenyl, cyano, nitro, —$NR_6R_7$, where $R_6$ and $R_7$, which may be the same or different, are hydrogen, straight or branched ($C_1$-$C_5$) alkyl, the —COOH group or one of its pharmaceutically acceptable esters; or the —$CONR_8R_9$ group, where $R_8$ and $R_9$, which may be the same or different, are hydrogen, straight or branched ($C_1$-$C_5$) alkyl; or $R_4$ is a ($C_6$-$C_{10}$) aroyl or ($C_6$-$C_{10}$) arylsulphonyl residue, optionally substituted with one or more groups selected from: halogen, hydroxy, straight or branched $C_1$-$C_5$ alkyl, straight or branched $C_1$-$C_5$ alkoxy, phenyl, cyano, nitro, —$NR_{10}R_{11}$, where $R_{10}$ and $R_{11}$, which may be the same or different, are hydrogen, straight or branched $C_1$-$C_5$ alkyl; or $R_4$ is a polyaminoalkyl substituent; or $R_4$ is a glycosyl substituent; $R_5$ is hydrogen, straight or branched $C_1$-$C_5$ alkyl, straight or branched $C_1$-$C_5$ alkenyl, $C_3$-$C_{10}$ cycloalkyl, straight or branched ($C_3$-$C_{10}$) cycloalkyl-($C_1$-$C_5$) alkyl, $C_6$-$C_{14}$ aryl, straight or branched ($C_6$-$C_{14}$) aryl-($C_1$-$C_5$) alkyl;

$R_2$ and $R_3$, which may be the same or different, are hydrogen, hydroxyl, straight or branched $C_1$-$C_5$ alkoxy; and the N1-oxides, the racemic mixtures, their individual enantiomers, their individual diastereoisomers, their mixtures, and pharmaceutically acceptable salts.

2. A compound according to claim 1, selected from the group consisting of:

20-O-(benzylglycyl)succinyl-camptothecin,

20-O-(tert-butylglycyl)succinyl-camptothecin bromide, 7-tert-butoxyiminomethyl-20-O-(tert-butylglycyl)succinyl-camptothecin, 20-O-(glycyl)succinyl-camptothecin, 20-O-(2-methoxyphenylglycyl)succinyl-camptothecin, and 7-tert-butoxyiminomethyl-20-O-(2-methoxyphenylglycyl)succinyl-camptothecin.

3. A process for the preparation of a compound according to claim 1, where n and m are 1, comprising:

a) reaction of the camptothecin, substituted with the $R_1$ group as defined above and optionally substituted with the $R_2$ and $R_3$ groups defined above, with a carboxylic acid with 3 to 11 carbon atoms, to obtain the respective hemiester in position 20; and b) transformation of the free carboxylic group of the hemiester in position 20 with an amino acid to give the respective amide —NH—Y.

4. A pharmaceutical composition containing a therapeutically effective amount of at least one compound according to claim 1, in admixture with pharmaceutically acceptable vehicles and excipients.

5. A compound according to claim 1, in which B is glycine, alanine, phenylalanine, valine, leucine, isoleucine, aspartic acid, glutamic acid, lysine, arginine, tyrosine, and γ-aminobutyric acid or a salt on a free carboxyl and/or on a free basic group with pharmaceutically acceptable base or acid.

6. A method of treating a tumor comprising administering to a subject having a tumor an effective amount of a compound of claim 1 wherein the tumor is selected from the group consisting of lung tumor, colorectal tumor, prostate tumor and glioma.

* * * * *